United States Patent [19]

Michaels

[11] 4,207,893
[45] Jun. 17, 1980

[54] DEVICE USING HYDROPHILIC POLYMER FOR DELIVERING DRUG TO BIOLOGICAL ENVIRONMENT

[75] Inventor: Alan S. Michaels, San Francisco, Calif.

[73] Assignee: Alza Corporation, Palo Alto, Calif.

[21] Appl. No.: 972,958

[22] Filed: Dec. 26, 1978

Related U.S. Application Data

[62] Division of Ser. No. 828,473, Aug. 29, 1977.

[51] Int. Cl.² .................................................. A61M 31/00
[52] U.S. Cl. .................................................. 128/260
[58] Field of Search .................... 128/213 R, 232, 260, 128/261-262, 271; 424/14, 25, 27

[56] References Cited

U.S. PATENT DOCUMENTS

| | | | |
|---|---|---|---|
| 3,760,805 | 9/1973 | Higuchi | 128/213 |
| 3,760,984 | 9/1973 | Theeuwes | 128/260 |
| 3,865,108 | 2/1975 | Hartop | 128/260 |
| 3,971,376 | 7/1976 | Whichterle | 128/260 |
| 3,987,760 | 10/1976 | Eckenhoff et al. | 128/260 |
| 3,995,631 | 12/1976 | Higuchi | 128/260 |

Primary Examiner—Robert W. Michell
Assistant Examiner—C. F. Rosenbaum
Attorney, Agent, or Firm—Paul L. Sabatine; Thomas E. Ciotti; Edward L. Mandell

[57] ABSTRACT

A self-powered device for delivering drug is disclosed. The device comprises (1) a substantially rigid housing, (2) a collapsible container storing a drug and having a passageway for delivering the drug in the housing, and (3) an expandable laminate positioned between the housing and the container. The laminate comprises (a) a lamina formed of an absorbent material laminated to (b) a lamina placed adjacent to the container and formed of a swellable hydrophilic polymer. In operation, when the device is in a biological environment, fluid from the environment is imbibed by the laminate into the housing causing the laminate to expand and exert pressure on the container, thereby collapsing the container and concomitantly pumping drug through the passageway from the device at a correspondingly controlled rate over a prolonged period of time.

5 Claims, 3 Drawing Figures

DEVICE USING HYDROPHILIC POLYMER FOR DELIVERING DRUG TO BIOLOGICAL ENVIRONMENT

CROSS-REFERENCE TO RELATED APPLICATION

This application is a division of U.S. Pat. application Ser. No. 828,473 filed on Aug. 29, 1977, which is incorporated herein by reference, and benefit is claimed of its filing date. These applications are assigned to the ALZA Corporation of Palo Alto, California.

FIELD OF THE INVENTION

This invention pertains to a self-powered, integrated device for delivering drug. More particularly, the invention relates to a device that is simple in construction and delivers drug in response to force applied by a swellable hydrophilic polymer on a container storing drug. The force causes the container to continuously collapse and decrease its internal volume, thereby propelling drug from the device.

BACKGROUND OF THE INVENTION

In recent times, much effort has been devoted to developing new and useful devices for delivering drugs to a drug receptor site. Generally, these devices deliver a drug by diffusion from a non-erodible polymer matrix, by release from an erodible polymer matrix, or by delivery from an osmotic device. While, these devices are useful, serious shortcomings are associated with their use. For example, devices which contain drug dispersed or dissolved in a non-erodible matrix often do not exhibit zero order drug release kinetics since the drug is first removed only from the surface layers of the matrix and the distance drug must diffuse to the surface from within the matrix increases with time. For this kind of a device, essentially $t^{-\frac{1}{2}}$ kinetics are observed. A serious shortcoming for devices made from an erodible polymer is in the polymer's inability to dissolve or erode at a uniform rate over time. Correspondingly, for these devices, drug is not delivered to the receptor at a uniform rate over time. One shortcoming observed for osmotic devices is the need for the drug to be soluble in fluid imbibed into the device, since a drug that cannot act as its own osmotically effective solute will not imbibe fluid, and without imbibition, drug is not pumped from the device. In view of the above presentation, it will be appreciated by those versed in the art that a critical need exists for a drug delivery device that is simple in construction, easy to make, and can deliver drug at a controlled rate over time to a drug receptor site.

OBJECTS OF THE INVENTION

Accordingly, it is an immediate object of this invention to make available a new and useful drug delivery device that overcomes the shortcomings known to the prior art.

Another object of the invention is to provide a drug delivery device that is simple in construction and which device exhibits all of the practical benefits of controlled and continuous administration of various drugs to animals and humans over a prolonged period of time.

Yet another object of the invention resides in the provision of an improved device which enables high concentrations of active drug to be administered therefrom, and which concentrations of drug will not exhibit the tendency to be leached from the device, nor be decreased in potency when the device is administering drug to a receptor.

Still another object of the invention is to provide a drug delivery device that is easy to manufacture and will release drug in solution, gel or semi-solid formulation, at a controlled rate over a prolonged period of time.

Other objects, features and advantages of this invention will become more apparent from the following description when taken in conjunction with the accompanying specification, drawings and the claims.

SUMMARY OF THE INVENTION

The invention concerns a device for delivering drug to a biological environment of use. The device comprises an expandable laminate surrounding a collapsible container filled with drug and positioned in a rigid housing member. In operation, the device releases drug in response to the laminate imbibing fluid and expanding, thereby exerting pressure on the container, which then collapses and urges drug from the device.

BRIEF DESCRIPTION OF THE DRAWINGS

In the drawings, which are not drawn to scale, but are set forth to illustrate various embodiments of the invention, the figures are as follows.

In the drawings and specification, like parts in related Figures are identified by like numbers. The terms appearing earlier in the specification and in the description of the drawings as well as embodiments thereof, are further described elsewhere in the disclosure.

DETAILED DESCRIPTION OF THE DRAWINGS

Figure 1:
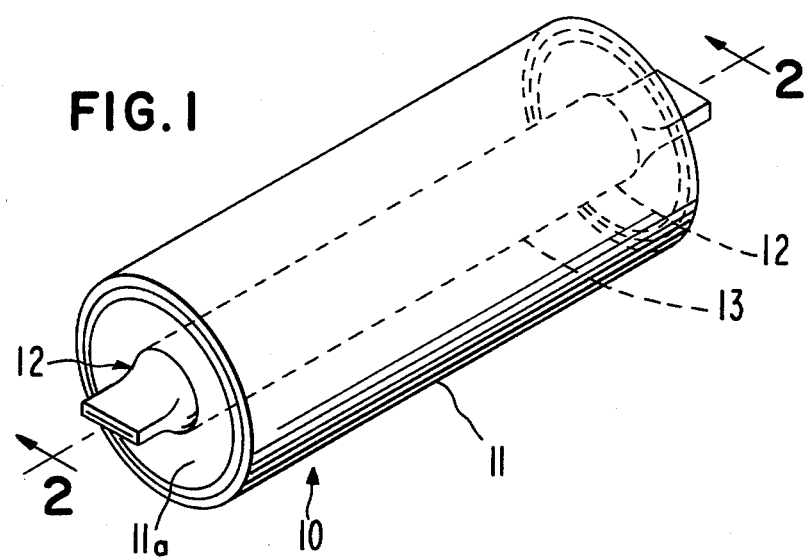
FIG. 1 is a front view of a dispensing device made according to the invention.

Turning now to the drawings in detail, which are an example of a new and useful device for dispensing a drug, and which example is not to be construed as limiting, one device is indicated in FIG. 1 by numeral 10. In FIG. 1, device 10 consists essentially of a housing 11 shaped, sized and adapted for placement in an environment of use. Housing 11 is made of a substantially rigid wall forming material, which wall surrounds and defines an internal space for receiving a container 12. Housing 11 has at least one opening 11a or it can have more than one opening through which container 12 communicates with the exterior of device 10. A detailed discussion of this and other materials used for manufacturing device 10, including drugs that can be dispensed by device 10, is presented later in this application. Device 10 comprises a container 12 placed within housing 11 for storing drug, which container 12 is seen in dashed lines in FIG. 1 and it is formed of a material that collapses in response to pressure applied against the exterior surface 13 of container 12.

Figure 2:
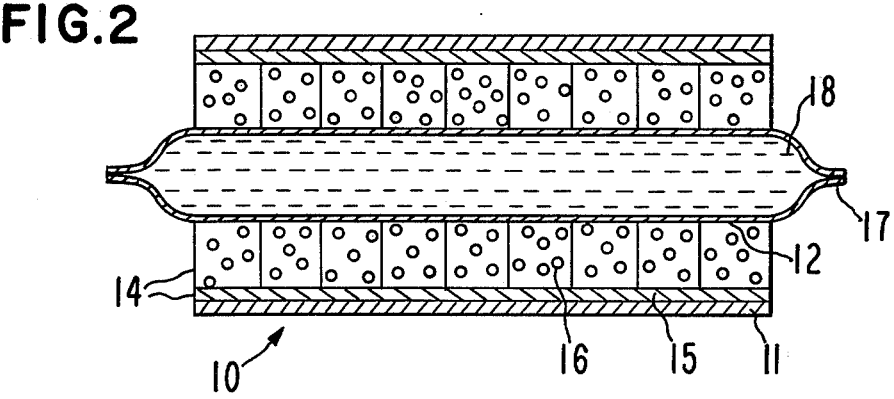
FIG. 2 is a cross-sectional view of the device of FIG. 1 through 2—2 thereof illustrating the structure of the device; and, FIG. 3 is an illustration of the device of FIG. 1 and 2 depicting the device in operation and dispensing drug therefrom.

Referring to FIG. 2, dispensing device 10 of FIG. 1 is seen in cross-section along line 2—2 of FIG. 1. As seen in FIG. 2, device 10 comprises a housing 11 or body member formed of a substantially shape-retaining rigid material having positioned within container 12. Container 12 is surrounded by a laminate 14 comprising lamina 15 and lamina 16. Lamina 15 is positioned adjacent to the interior surface of housing 11 distant from container 12, and it, 15, is formed of an absorbent porous or fibrous material capable of imbibing external fluid into housing 11. Fluid can enter device 10 through opening 11a or in another embodiment it can enter through one or a multiplicity of passageways or holes in housing 11. Lamina 16 is in laminar arrangement with lamina 15, and lamina 16 is positioned adjacent to the exterior surface 13 of container 12, distant from housing 11. Lamina 16 is formed of a swellable hydrophilic polymeric material that can imbibe fluid present in housing 11 for increasing its space-occupying dimensions. Container 12 is formed of an elastomeric (or other low-modulus) material and it, 12, has a passageway 17 for dispensing drug 18 from device 10 to a biological environment of use. Passageway 17, in one embodiment, is formed by the wall of container 12 terminating in passageway 17 which is projected through opening 11a in housing 11. In another embodiment, not shown, passageway 17 is an aperture in the wall of container 12 and it connects to a conduit or tube extended through opening 11a for releasing drug 16 from device 10.

Figure 3:
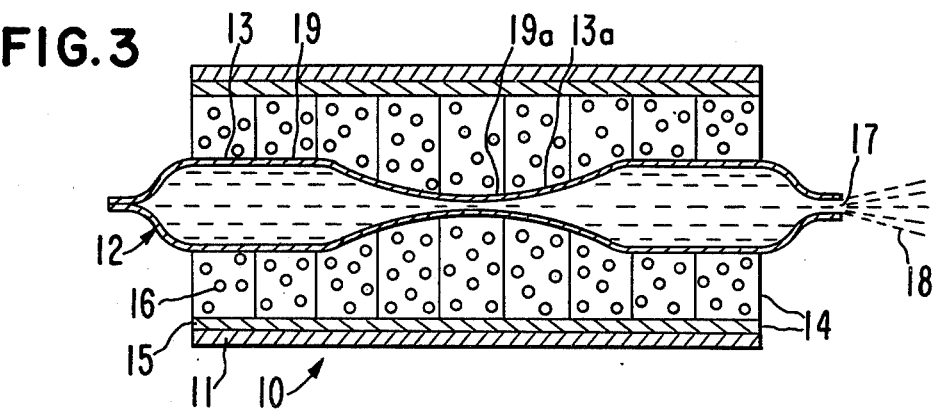

In FIG. 3, device 10 is seen dispensing drug 18 through passageway 17 from container 12. In operation, device 10 functions by laminate 14 comprised of lamina 15 and lamina 16 slowly imbibing water or biological fluid into laminate 14, causing lamina 16 to swell and expand from position 19 to 19a, thereby exerting pressure against container 12. The pressure applied against the entire exterior surface 13 of container 12 causes surface 13 to slowly collapse to position 13a. The collapse of surface 13 correspondingly decreases the internal volume of container 12 thereby expelling drug 13 at a predetermined and controlled rate through passageway 17 to the environment of use over a prolonged period of time. The size of passageway 17 can in an optional embodiment be given predetermined dimensions as an additional aid for controlling the rate of drug release by device 10.

While FIGS. 1 through 3 are illustrative of various devices that can be made according to the invention, and it is to be understood these devices are not to be construed as limiting, as they can take a wide variety of shapes, sizes and forms for delivering drug to varied and many different environments of use. For example, device 10 can be manufactured for dispensing drug 18 to animals, including warm-blooded mammals, humans, household, farm, sport and zoo animals. Device 10 can be made for dispensing drug 18 to body cavities and body openings such as for oral administration, for use as intramuscular implants, intrauterine, vaginal, cervical, rectal, nasal, ear, and dermal devices. Device 10 also can be made for use as an artificial gland and for arterial and venous administration of drug 18. The device can be made for use in homes, hospitals,, nursing homes and clinics.

DETAILED DESCRIPTION OF THE INVENTION

Device 10, as used for the purpose of this invention consists of a housing 11 made of a substantially rigid polymer material. This material permits pressure to be exerted against it without any major change in its shape or dimensions, thereby assuring that pressure generated in device 10 is exerted against container 12. Housing 11 can optionally be formed of a member selected from the group consisting of an impermeable material with at least one opening, a permeable material, a microporous material, and the like. Representative polymers suitable for forming housing 11 include polyethylene, polypropylene, polytetrafluoroethylene, polyamides, polyformaldehyde, polystyrene, polycarbonate, polyacrylate, polymethacrylate, polyacrylonitrile, polyvinylchloride, and the like. Generally, the thickness of housing 11 will vary depending on the device and its use, and it will usually have a thickness of 1 mm to 50 mm or more.

Representative of absorbent materials suitable for forming lamina 15 are porous materials derived from animal and plant origins including wool, cotton, straw, flax and other vegetable fibers. Exemplary materials include cotton mats or pads of fibers, artificial regenerated cellulose sponge, blotting paper, tea bag paper, and matted, felted, porous or fibrous sheets, or other means such as absorbent bleached and unbleached paper. The thickness of lamina 15 will vary depending on the device, and it will usually have a range of 0.50 mm to 50 mm, or more.

Representative of swellable hydrophilic polymers suitable for forming lamina 16 are, for example, lightly cross-linked predominantly linear polymers covalently or ionically cross-linked, (such cross-links being formed by covalent or ionic bonds), which interact with biological and other aqueous solutions by swelling or expanding to some equilibrium state. These polymers swell or expand to a very high degree without dissolution, usually exhibiting a 5 to 50 fold volume increase. Materials for this purpose include poly(hydroxyalkyl methacrylates), poly(N-vinyl-2-pyrrolidone), anionic and cationic hydrogels, polyelectrolyte complexes, poly(vinyl alcohol) having a low acetate residual and cross-linked with glyoxal, formaldehyde, or glutaraldehyde, methylcellulose cross-linked with a dialdehyde, a mixture of agar and sodium carboxymethyl cellulose, a water-insoluble, water-swellable copolymer produced by forming a dispersion of finely divided copolymer of maleic anhydride with styrene, ethylene, propylene, butylene or isobutylene cross-linked with from about 0.001 to about 0.5 mole of a polyunsaturated cross-linking agent per mole of maleic anhydride in the copolymer as disclosed in U.S. Pat. No. 3,989,586, water-swellable polymers of N-vinyl lactams as disclosed in U.S. Pat. No. 3,992,562, and the like. Generally, the lamina 16 will have a thickness of about 5 mm to 50 mm, or higher, and in a presently preferred embodiment it will have an expanded or swelled thickness state approximately equal to the internal diameter of container 12 to produce a complete collapse of container 12 and discharge of drug 18 therefrom.

Representative materials suitable for manufacturing container 12 are materials that can be designed into a shaped container, elastomeric tube or capsule, which collapses in response to externally applied pressure, thereby dispensing drug. Typical elastomeric polymers include natural rubber often identified by the synonyms poly(2-methyl-1,3-butadiene) and cis-1,4-polyisoprene, gutta percha or trans-polyisoprene, cyclised rubber, synthetic isoprene rubber, butadiene rubber, styrene-butadiene rubbers, nitrile rubber, chloroprene rubbers, ethylene-propylene rubbers, butyl rubbers and the like as disclosed in *Handbook of Common Polymers*, by Scott and Roff, Sections 29 through 40, 1971, published by the Chemical Rubber Company, Cleveland, Ohio. Container 12, formed of the above representative materials, can have its wall of varying thickness, usually about 2 mm to 50 mm, or more depending on the container and its use. Container 12 can be manufactured with one or more passageways for dispensing drug, or it can be made to form a passageway when the device is in the environment of use. In this embodiment, one end of container 12 is closed with a water-soluble plug of an erodible material, such as polyvinyl alcohol, gelatin, or the like that erodes in the environment of use to form a small-diameter orifice. In another embodiment, a preformed orifice having a cross-section of 1 to 10 mils can be temporarily closed with a plug, which plug is ejected when the container collapses in use, thereby forming the orifice in situ.

Exemplary drugs that can be administered according to the spirit of the invention include locally and systemically acting drugs. These drugs include a member selected from the group consisting of physiologically and pharmacologically acting drugs such as gastrointestinal administrable drugs, central nervous system acting drugs, hypnotic, sedative, psychic energizer, tranquilizer, anticonvulsant, antiparkinson, muscle relaxant, analgesic, antipyretic, anti-inflammatory, anesthetic, antispasmodic, antimicrobial, antiviral, antiulcer, hormonal, sympathomimetic, diuretic, hypoglycemic, vitamins, anticontraceptive, and ophthalmic drugs. These beneficial drugs and their dose amount for humans are known to the art in *Drill's Pharmacology in Medicine*, edited by DiPalma, Joseph R., 1965, published by McGraw-Hill Book Company, New York, in *Pharmacological Basis of Therapeutics*, by Goodman and Gilman, 4th Edition, 1970, published by the MaMillian Co., London, and in U.S. Pat. No. 3,977,404, which patent is assigned to the ALZA Corporation of Palo Alto, California, the assignee of this patent application. The drug in the container can be mixed with a pharmaceutically acceptable liquid carrier such as water, saline, cottonseed oil, sesame oil, ethyl oleate, isopropyl myristate, propylene glycol and the like. The drug can be present in solution, in semi-solid or paste formulation, in a thixotropic state and the like, which permits controlled dispensing of drug from the device. Pharmaceutically acceptable carriers and the like are known to the art in *Remington's Pharmaceutical Sciences*, 14th Edition, pages 1461 to 1762, 1970, published by the Mack Publishing Company, Easton, Pennsylvania.

Representative examples of drugs that can be dispensed from an oral device comprising (1) a rigid polyethylene housing manufactured with an opening and having placed therein (2) a container shaped and sized like a 000 capsule with a single orifice for releasing drug and formed of natural rubber, which container is surrounded by (3) a monolithic laminate of polyvinyl alcohol cross-linked with glyoxal directly coated upon teabag paper without filling the pores of the paper, and a drug formulation in the container such as (4) tetracycline hydrochloride in polyethylene glycol 200, or (5) a formulation consisting of a suspension of 0.1 mg of digitoxin in a carrier medium of water, 17 weight percent, which formulation in either embodiment are dispensed at a controlled rate from the device, when the device is in the environment of use. In another embodiment, the housing is made with a multiplicity of holes for admitting fluid into the housing during the operation of the device.

Although the foregoing invention has been described in detail by way of illustration of a preferred embodiment and examples for purpose of clarity of understanding, it will be understood that certain changes and modifications may be practiced within the scope and spirit of the invention.

We claim:

1. A Drug delivery device comprising:
    (a) a drug
    (b) a housing having a shape-retaining wall defining an internal space and an opening connecting the space with the exterior of the device, said housing formed of a member selected from the group consisting of a fluid permeable and microporous polymers;
    (c) a container in the housing, the container consisting essentially of a collapsible wall surrounding a reservoir for storing the drug and a passageway that projects through the opening for delivering drug from the container to the exterior of the device, said container formed of a material selected from the group consisting of natural rubber, gutta, percha, cyclised rubber, synthetic rubber, isoprene rubber, butadiene rubber, styrene-butadiene rubber, nitrile rubber, chloroprene rubber and ethylene-propylene rubber;
    (d) a laminate in the housing, the laminate surrounding the container and comprising a lamina of an absorbent material and a lamina of a swellable hydrophilic polymer, said laminate capable of imbibing fluid into the housing through the polymer thereby causing the laminate to expand and exert pressure on the container which collapses said container and concomitantly pumps drug through the passageway from the device at a controlled rate over a prolonged period of time.

2. The drug delivery device according to claim 1, wherein the lamina formed of the absorbent material is formed of a member selected from the group consisting of wool, cotton, straw, flax, paper and mixtures thereof.

3. The drug delivery device according to claim 1, wherein the swellable hydrophilic polymer is cross-linked and it is a member selected from the group consisting of cross-linked poly(hydroxyalkyl methacrylate), poly(N-vinyl-2-pyrrolidone), polyelectrolyte complexes, poly(vinyl alcohol) cross-linked with glyoxal, formaldehyde or gluturaldehyde, and cross-linked cellulose.

4. The drug delivery device according to claim 1 wherein the drug is a member selected from the group consisting of locally and systemically acting gastrointestinal, nervous system, hypnotic, sedative, psychic energizer, tranquilzer, anticonvulsant, antiparkinson, muscle relaxant, analgesic, antipyretic, anti-inflammatory, anesthetic, antispasmodic, antimicrobial, antiviral, antiulcer, hormonal, sympthomimetic, diurectic, hypoglycemic, and anticontraceptive drugs.

5. The drug delivery device according to claim 14, wherein the drug in the container is mixed with a pharmaceutically acceptable carrier.

* * * * *